US008262693B2

(12) United States Patent
Pai et al.

(10) Patent No.: US 8,262,693 B2
(45) Date of Patent: Sep. 11, 2012

(54) APPARATUS AND METHODS FOR SEALING A VASCULAR PUNCTURE

(75) Inventors: Suresh S. Pai, Mountain View, CA (US); Celso J. Bagaoisan, Union City, CA (US); Farhad Khosravi, Los Altos Hills, CA (US)

(73) Assignee: AccessClosure, Inc., Mountain View, CA (US)

( * ) Notice: Subject to any disclaimer, the term of this patent is extended or adjusted under 35 U.S.C. 154(b) by 2005 days.

(21) Appl. No.: 10/982,385

(22) Filed: Nov. 5, 2004

(65) Prior Publication Data

US 2006/0100664 A1 May 11, 2006

(51) Int. Cl.
*A61B 17/03* (2006.01)

(52) U.S. Cl. ........................................................ 606/213

(58) Field of Classification Search .................. 606/213, 606/214, 217; 623/1.36
See application file for complete search history.

(56) References Cited

U.S. PATENT DOCUMENTS

| | | | |
|---|---|---|---|
| 2,115,492 | A | 4/1938 | Kober |
| 3,765,419 | A | 10/1973 | Usher |
| 4,002,173 | A | 1/1977 | Manning |
| 4,260,077 | A | 4/1981 | Schroeder |
| 4,327,709 | A | 5/1982 | Hanson et al. |
| 4,362,150 | A | 12/1982 | Lombardi, Jr. et al. |
| 4,472,542 | A | 9/1984 | Nambu |
| 4,540,404 | A | 9/1985 | Wolvek |
| 4,655,211 | A | 4/1987 | Sakamoto et al. |
| 4,664,857 | A | 5/1987 | Nambu |
| 4,734,097 | A | 3/1988 | Tanabe |
| 4,738,658 | A | 4/1988 | Magro et al. |
| 4,838,280 | A | 6/1989 | Haaga |
| 4,852,568 | A | 8/1989 | Kensey |
| 4,890,612 | A | 1/1990 | Kensey |
| 5,061,274 | A | 10/1991 | Kensey |
| 5,104,375 | A | 4/1992 | Wolf et al. |

(Continued)

FOREIGN PATENT DOCUMENTS

EP 0 476 178 A1 3/1992

(Continued)

OTHER PUBLICATIONS

PCT International Search Report for PCT/USUS2005/039693, Applicant: Accessclosure, Inc., Form PCT/ISA/210 and 220, dated Mar. 21, 2006 (6 pages). PCT Written Opinion for PCT/USUS2005/039693, Applicant: Accessclosure, Inc., Form PCT/ISA/237, dated Mar. 21, 2006 (6 pages).

*Primary Examiner* — Ryan Severson
(74) *Attorney, Agent, or Firm* — Vista IP Law Group LLP; William A. English

(57) ABSTRACT

Apparatus for sealing a puncture through tissue to a blood vessel includes a cartridge including a proximal end, a distal end sized for insertion into a puncture, and a lumen extending therebetween. A bioabsorbable plug is disposed within the lumen adjacent the distal end, and an anchoring element is disposed within the lumen proximal to the plug. A pusher member is disposed within the lumen for deploying the plug and anchoring element out the distal end of the cartridge. The plug may be formed from lyophilized hydrogel and the anchoring element may be formed from air-dried hydrogel, the anchoring element hydrating slower than the plug when exposed to an aqueous environment. During use, the plug and anchoring element are delivered into the puncture, the plug is cinched against the vessel wall. Protrusions on the anchoring element engage tissue surrounding the puncture to prevent proximal movement of the plug.

43 Claims, 8 Drawing Sheets

20 25 24 26 22 23 18 146 144 140 142 124 125 134 126 120 130 122 123 132 2 102 135 136 101 18

U.S. PATENT DOCUMENTS 5,104,389 A 4/1992 Deem et al.
5,108,421 A * 4/1992 Fowler .......................... 606/213
5,192,300 A 3/1993 Fowler
5,192,302 A 3/1993 Kensey et al.
5,221,259 A 6/1993 Weldom et al.
5,258,042 A 11/1993 Mehta
5,259,835 A 11/1993 Clark et al.
5,275,616 A 1/1994 Fowler
5,290,310 A 3/1994 Makower et al.
5,292,332 A 3/1994 Lee
5,306,254 A 4/1994 Nash et al.
5,320,639 A 6/1994 Rudnick
5,324,306 A 6/1994 Makower et al.
5,334,216 A * 8/1994 Vidal et al. .................... 606/213
5,370,660 A * 12/1994 Weinstein et al. ............ 606/213
5,383,896 A * 1/1995 Gershony et al. ............. 606/213
RE34,866 E 2/1995 Kensey et al.
5,391,183 A 2/1995 Janzen et al.
5,409,703 A 4/1995 McAnalley
5,413,571 A 5/1995 Katsaros et al.
5,419,765 A 5/1995 Weldon et al.
5,431,639 A 7/1995 Shaw
5,437,292 A 8/1995 Kipshidze et al.
5,437,631 A 8/1995 Janzen
5,441,517 A 8/1995 Kensey et al.
5,443,481 A 8/1995 Lee
5,464,396 A 11/1995 Barta et al.
5,486,195 A 1/1996 Myers et al.
5,489,278 A 2/1996 Abrahamson
5,514,158 A 5/1996 Kanesaka
5,529,577 A 6/1996 Hammerslag
5,531,759 A * 7/1996 Kensey et al. ................ 606/213
5,550,187 A 8/1996 Rhee
5,571,181 A 11/1996 Li
5,580,923 A 12/1996 Yeung
5,591,204 A 1/1997 Jansen et al.
5,591,205 A 1/1997 Fowler
5,601,602 A 2/1997 Fowler
5,626,601 A 5/1997 Gershony et al.
5,637,086 A 6/1997 Ferguson et al.
5,643,464 A 7/1997 Rhee et al.
5,660,849 A 8/1997 Polson et al.
5,700,277 A * 12/1997 Nash et al. .................... 606/213
5,700,477 A 12/1997 Rosenthal
5,716,375 A 2/1998 Fowler
5,718,916 A 2/1998 Scherr
5,725,498 A 3/1998 Janzen et al.
5,725,551 A 3/1998 Myers et al.
5,728,122 A 3/1998 Leschinsky et al.
5,731,368 A 3/1998 Stanley et al.
5,741,223 A 4/1998 Janzen et al.
5,744,153 A 4/1998 Yewey et al.
5,752,974 A 5/1998 Rhee et al.
5,780,044 A 7/1998 Yewey et al.
5,782,860 A 7/1998 Epstein et al.
5,785,679 A 7/1998 Abolfathi et al.
5,795,331 A 8/1998 Cragg et al.
5,830,130 A 11/1998 Janzen et al.
5,836,970 A 11/1998 Pandit
5,843,124 A 12/1998 Hammerslag
5,916,236 A 6/1999 Muijs Van de Moer et al.
5,922,009 A 7/1999 Epstein et al.
5,928,266 A 7/1999 Kontos
5,941,847 A 8/1999 Huber et al.
5,948,429 A 9/1999 Bell
5,948,829 A 9/1999 Wallajapet
5,951,583 A 9/1999 Jensen et al.
5,951,589 A 9/1999 Epstein et al.
5,957,952 A 9/1999 Gershony
5,972,375 A 10/1999 Truter
5,973,014 A 10/1999 Funk
6,017,359 A 1/2000 Gershony et al.
6,022,361 A 2/2000 Epstein et al.
6,027,471 A 2/2000 Fallon et al.
6,045,570 A 4/2000 Epstein et al.
6,048,358 A 4/2000 Barak
6,051,248 A 4/2000 Sawhney et al.
6,056,768 A 5/2000 Cates
6,056,769 A 5/2000 Epstein et al.
6,063,061 A 5/2000 Wallace
6,083,522 A 7/2000 Chu
6,152,943 A 11/2000 Sawhney
6,162,240 A * 12/2000 Cates et al. .................. 606/213
6,162,241 A 12/2000 Coury et al.
6,165,201 A 12/2000 Sawhney
6,179,862 B1 1/2001 Sawhney
6,238,412 B1 5/2001 Dubrul et al.
6,271,278 B1 8/2001 Park
6,287,323 B1 9/2001 Hammerslag
6,296,658 B1 10/2001 Gershony
6,299,597 B1 10/2001 Buscemi et al.
6,302,898 B1 10/2001 Edwards et al.
6,350,274 B1 2/2002 Li
6,368,300 B1 4/2002 Fallon et al.
6,371,975 B2 4/2002 Cruise et al.
6,379,373 B1 4/2002 Sawhney
6,458,147 B1 10/2002 Cruise et al.
6,475,177 B1 11/2002 Suzuki
6,514,534 B1 2/2003 Sawhney
6,562,059 B2 5/2003 Edwards et al.
6,566,406 B1 5/2003 Pathak
6,569,185 B2 5/2003 Ungs
6,605,294 B2 * 8/2003 Sawhney ...................... 424/426
6,608,117 B1 8/2003 Gvozdic
6,613,070 B2 9/2003 Redmond et al.
6,635,068 B1 10/2003 Dubrul et al.
6,689,148 B2 2/2004 Sawhney
6,699,261 B1 3/2004 Cates et al.
6,703,047 B2 3/2004 Sawhney
6,774,151 B2 8/2004 Malmgren
6,818,008 B1 11/2004 Cates
6,818,018 B1 11/2004 Sawhney
6,863,924 B2 3/2005 Ranganathan
6,887,974 B2 5/2005 Pathak
6,960,617 B2 11/2005 Omidian
2001/0031948 A1 10/2001 Cruise et al.
2001/0046518 A1 11/2001 Sawhney
2001/0047187 A1 11/2001 Milo et al.
2001/0051813 A1 12/2001 Hnojewyj
2002/0015724 A1 2/2002 Yang et al.
2002/0026215 A1 * 2/2002 Redmond et al. ............. 606/213
2002/0062104 A1 5/2002 Ashby et al.
2002/0072767 A1 * 6/2002 Zhu ............................... 606/213
2002/0106409 A1 8/2002 Sawhney et al.
2002/0111392 A1 8/2002 Cruise
2002/0111651 A1 8/2002 Ungs
2002/0188319 A1 12/2002 Morris et al.
2003/0008831 A1 1/2003 Yang et al.
2003/0012734 A1 1/2003 Pathak
2003/0051735 A1 3/2003 Pavcnik et al.
2003/0088269 A1 5/2003 Ashby
2003/0088271 A1 5/2003 Cragg et al.
2003/0135234 A1 7/2003 Fisher et al.
2003/0135235 A1 7/2003 Fisher et al.
2003/0135236 A1 7/2003 Fisher et al.
2003/0139770 A1 7/2003 Fisher et al.
2003/0139771 A1 7/2003 Fisher et al.
2003/0139772 A1 7/2003 Fisher et al.
2003/0139773 A1 7/2003 Fisher et al.
2003/0233120 A1 12/2003 Akerfeldt
2004/0122350 A1 6/2004 Zhong et al.
2004/0147016 A1 7/2004 Rowley
2004/0249342 A1 12/2004 Khosravi
2004/0254636 A1 * 12/2004 Flagle et al. ................. 623/1.24
2005/0119737 A1 * 6/2005 Bene et al. ..................... 623/4.1

FOREIGN PATENT DOCUMENTS

EP 0 482 350 B1 4/1992
WO WO 92/22252 12/1992
WO 0014155 3/2000
WO 0019912 4/2000
WO WO 00/19912 4/2000
WO 03094749 11/2003

* cited by examiner

APPARATUS AND METHODS FOR SEALING A VASCULAR PUNCTURE

FIELD OF THE INVENTION

The present invention relates generally to apparatus and methods for sealing punctures in a body, and more particularly, to apparatus and methods for sealing a vascular puncture extending through tissue into a blood vessel, and to apparatus and methods for delivering a plug into a percutaneous puncture extending from a patient's skin to a blood vessel or other body lumen to seal the puncture.

BACKGROUND

Apparatus and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators.

A catheter or other device may be advanced through the introducer sheath and over the guide wire into a position for performing a medical procedure. Thus, the introducer sheath may facilitate accessing and/or introducing various devices into the vessel, while minimizing trauma to the vessel wall and/or minimizing blood loss. Upon completing the procedure, the device(s) and introducer sheath may be removed, leaving a puncture extending between the skin and the vessel wall.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

Various apparatus and methods have been suggested for sealing a percutaneous puncture instead of using external pressure. For example, U.S. Pat. No. 5,108,421 to Fowler discloses a plug that may be delivered into a puncture through tissue. The plug is a cylindrical rod-shaped member which is constructed of a porous, bioabsorbable and expandable hemostatic collagen sponge or a polymerized polylactic acid or polyglycolic acid. In one embodiment, a catheter is inserted through the puncture into the blood vessel. A balloon on the catheter is expanded and retracted until the balloon is disposed adjacent the puncture at the wall of the vessel. The plug may be advanced into the puncture until the plug contacts the balloon. Once the plug is positioned within the puncture, the balloon may be deflated and withdrawn, leaving the plug within the puncture to expand and seal the puncture and/or to promote hemostasis.

Alternatively, U.S. Pat. Nos. 5,192,302 and 5,222,974 issued to Kensey et al. describe a bioabsorbable collagen plug that may be delivered through an introducer sheath into a puncture site. The disclosed plug, however, may be difficult to position properly with respect to the vessel, which may be significant since it is generally undesirable to expose the collagen material within the bloodstream where it may float downstream and cause an embolism.

U.S. Pat. No. 6,605,295 describes rods, plugs, crushed or irregularly shaped pieces of substantially dehydrated hydrogel that may be introduced into a lumen or void in a patient's body to seal or plug a biopsy needle track, reinforce weak tissue, or deliver a therapeutic compound. In one embodiment, a plug of dehydrated hydrogel may be deployed into the site of an arteriotomy and allowed to hydrate in the presence of the tissue fluids and blood, to fill the track of the catheter sheath and prevent further bleeding. By swelling to equilibrium hydration, the plug may lock itself firmly in place and thus reduce the risk of formation of a large hematoma at the site of the puncture.

U.S. Pat. No. 6,703,047 discloses dehydrated hydrogel precursor-based, tissue adherent compositions. The hydrogels may be used, for example, for sealing fluid leaks from tissue, as adherent drug delivery depots, and as means for augmenting and/or supporting tissue. The hydrogels may be administered directly to an open wound site or may be dispensed, e.g., using a non-adhesive backing material, an absorbable backing material, a syringe applicator, a powder atomization or aerosolization system, or a needle-less injector.

SUMMARY OF THE INVENTION

The present invention is directed to apparatus and methods for sealing a puncture in a body, and, more particularly, to apparatus and methods for providing temporary or permanent hemostasis within a vascular puncture extending into a blood vessel, and/or to apparatus and methods for delivering a sealing plug into a percutaneous puncture extending from a patient's skin to a blood vessel or other body lumen.

In accordance with one embodiment, an apparatus is provided for sealing a puncture extending through tissue that includes a tubular member including a proximal end, a distal end sized for insertion through the puncture, a lumen extending between the proximal and distal ends, and a distal opening in communication with the lumen. A bioabsorbable plug is disposed within the lumen, e.g., adjacent the distal opening, and a bioabsorbable anchor element is disposed within the lumen proximal to the plug. A pusher member is slidable within the lumen of the tubular member for deploying the plug and anchor element through the lumen and out the distal opening of the tubular member.

In one embodiment, the plug and anchoring element may include material, hydrogel material, that hydrates when exposed to an aqueous physiological environment, the plug hydrating at a more rapid rate than the anchoring element. In addition or alternatively, the plug may be porous and the anchoring element may be the anchoring element may be less porous than the plug. In an exemplary embodiment, the anchoring element may include a substantially rigid body, e.g., formed from air-dried hydrogel, and may include one or more protrusions for securing the anchoring element to surrounding tissue within a puncture.

In exemplary embodiments, the plug may include a core, e.g., of lyophilized hydrogel, and a coating on at least a portion of the core, e.g., including first and second precursors, that remains in an unreactive state prior to exposure to an aqueous physiological environment in the tissue whereupon the first and second precursors react to form an adherent coating on the core. Optionally, an activating agent, e.g., a pH adjusting material, may be disposed on at least a portion of the core, the activating agent facilitating or initiating reaction of the first and second precursors when exposed to an aqueous physiological environment.

In accordance with another embodiment, an apparatus is provided for sealing a puncture extending through tissue and communicating with a body lumen that includes a tubular member including a proximal end, a distal end sized for insertion through the puncture and into the body lumen, and a lumen extending between the proximal and distal ends. A bioabsorbable plug may be disposed within the lumen of the tubular member adjacent the distal end and a bioabsorbable anchoring element may be disposed within the lumen of the tubular member proximal to the plug. A pusher member may be movable within the tubular member lumen for deploying the plug and anchoring element out the distal end of the tubular member.

The pusher member, plug, and anchoring element may include a lumen extending therethrough, and the apparatus may include an elongate positioning member including a proximal end slidable through the plug lumen, the anchoring element lumen, and the pusher member lumen. The positioning member may include a positioning element on a distal end thereof for preventing the positioning element from being removed from the body lumen into the puncture after being deployed within the body lumen and/or for sealing the body lumen from the puncture.

In accordance with still another embodiment, a method is provided for sealing a puncture extending through tissue to a body lumen. A positioning member may be introduced into the puncture until a positioning element thereon is disposed within the body lumen, and the positioning member may be retracted until the positioning element contacts a wall of the body lumen.

A bioabsorbable plug may be delivered into the puncture over the positioning member until the plug is disposed proximate the positioning element, and an anchoring element may be delivered into the puncture above the plug to prevent the plug from moving proximally within the puncture.

In one embodiment, the plug and anchoring element are carried within a tubular member, and the plug and anchoring element may be delivered into the puncture simultaneously by advancing the tubular member into the puncture. The tubular member may be retracted while maintaining the plug and the anchoring element within the puncture to expose the plug and the anchoring element within the puncture, e.g., adjacent the body lumen. Optionally, the plug may be cinched or otherwise compressed against a wall of the body lumen.

When the plug and/or anchoring element are exposed to bodily fluid when the tubular member is retracted, the plug and/or anchoring element may hydrate to enhance sealing the puncture. For example, the plug and the anchoring element may include hydrogel material, the anchoring element hydrating more slowly than the plug when exposed within the puncture. Optionally, a sealing compound, e.g., a liquid hydrogel, may be delivered into the puncture after delivering the plug into the puncture, e.g., to enhance sealing the puncture.

Other aspects and features of the present invention will become apparent from consideration of the following description taken in conjunction with the accompanying drawings.

DETAILED DESCRIPTION OF THE PREFERRED EMBODIMENTS

Figure 1:
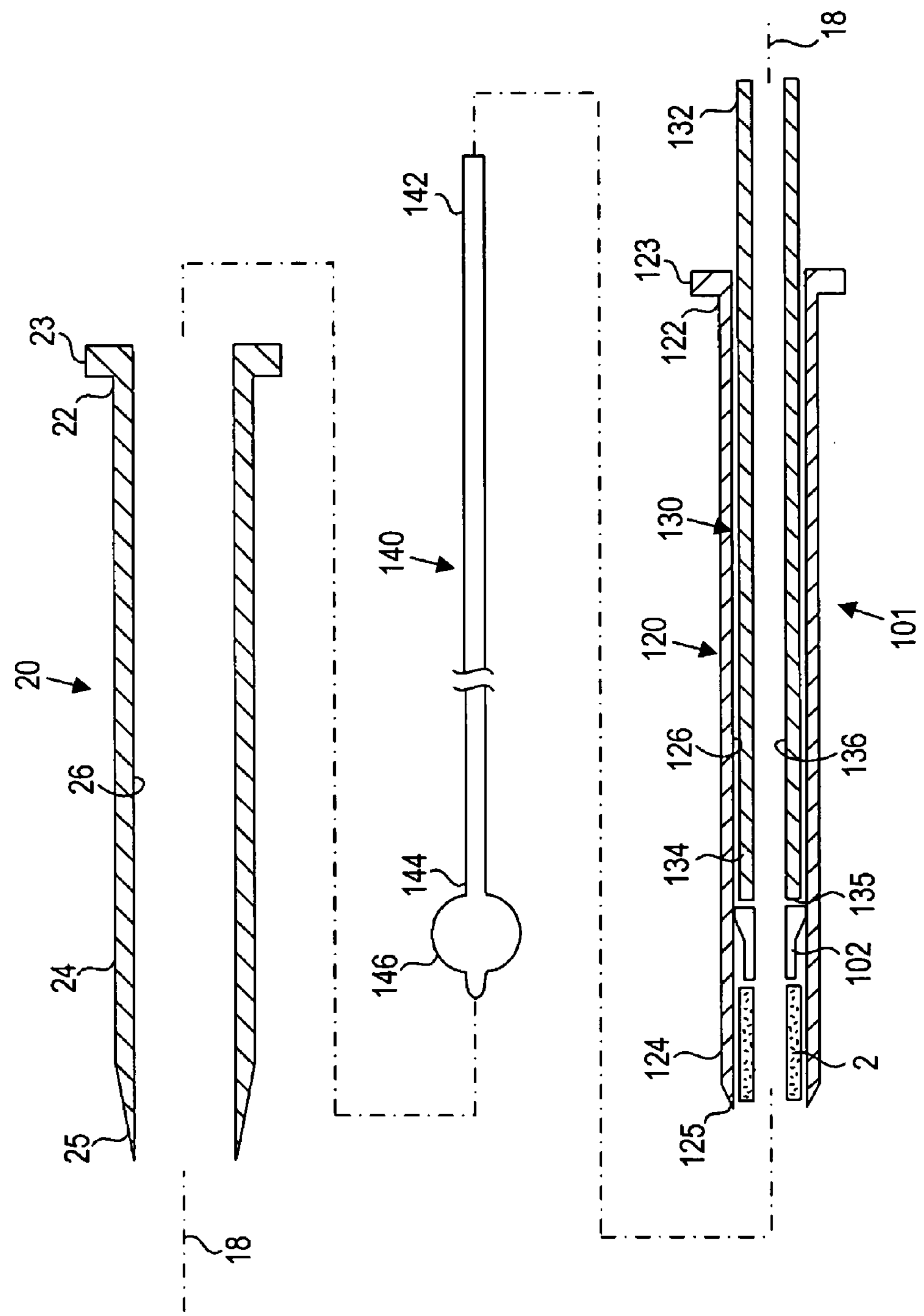
FIG. 1 is an exploded side view of an apparatus for delivering a plug into a puncture through tissue.
Figure 2A:
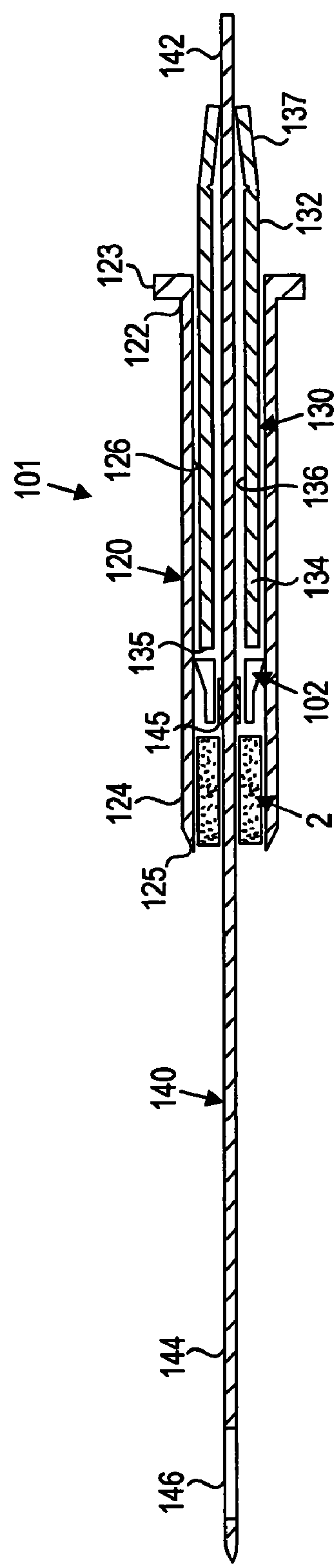
FIGS. 2A and 2B are cross-sectional views of the apparatus of FIG. 1, with a cartridge carrying a plug and anchor in proximal and distal positions, respectively.
Figure 2B:
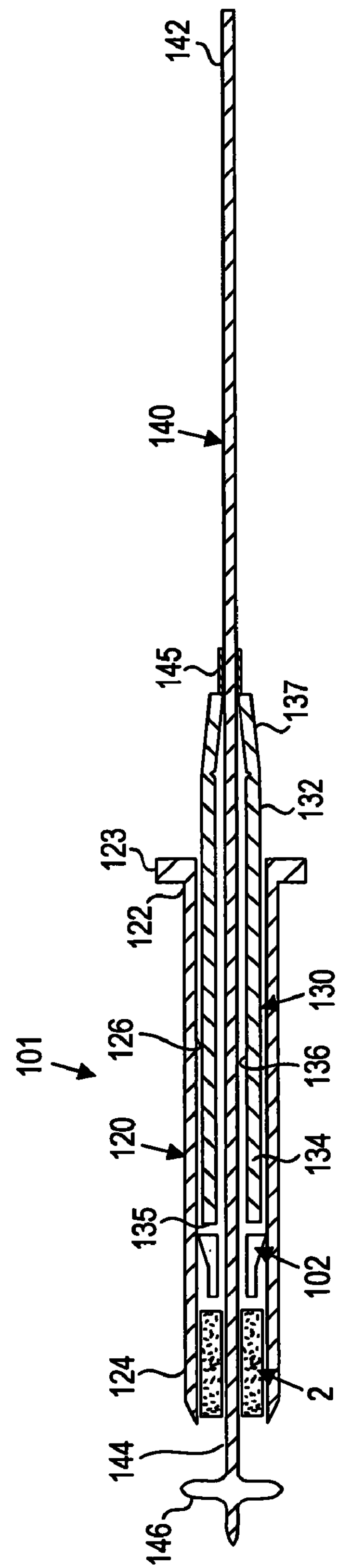

Turning to the drawings, FIGS. 1, 2A, and 2B show an exemplary embodiment of an apparatus 101 for sealing a puncture through tissue. Generally, the apparatus 101 includes a cartridge or other tubular member 120 and a plunger, cincher, or other pusher member 130. The cartridge 120 generally carries a plug 2 and an anchoring element 102, such as those described further below. In addition, the apparatus 101 may include a positioning member 140, a delivery, access, or introducer sheath 20, and/or other components, e.g., a needle and/or guidewire for creating a puncture (not shown), and/or a source of sealing compound (also not shown).

The introducer sheath 20 may be a substantially rigid, semi-rigid, and/or flexible tubular body, including a proximal end 22, a distal end 24 sized for insertion into a puncture through tissue, and a lumen 26 extending between the proximal and distal ends 22, 24. The distal end 24 may be tapered and/or may include a substantially atraumatic distal tip 25 for facilitating advancement through a puncture. The introducer sheath 20 may include a handle or hub 23 on the proximal end 22, and/or one or more seals on the proximal end 22, e.g., a hemostatic seal (not shown) that prevents proximal flow of blood or other fluids, yet accommodates inserting one or more instruments (also not shown) into the lumen 26 of the introducer sheath 20.

The cartridge 120 may be an elongate tubular body including a proximal end 122, a distal end 124, and a lumen 126 extending between the proximal and distal ends 122, 124. The cartridge 120 may include a tapered distal tip 125 and/or an enlarged handle or hub 123 on the proximal end 122. The cartridge 120 may be substantially rigid, semi-rigid, or flexible, e.g., such that the cartridge 120 may be advanced through the introducer sheath 20 or otherwise into a puncture through tissue.

The pusher member 130 may also be an elongate tubular body, e.g., a plunger or catheter, including a proximal end 132, a distal end 134, and a lumen 136 extending between the proximal and distal ends 132, 134. The pusher member 130 may have a size for slidable insertion into the lumen 126 of the cartridge 120. The distal end 134 of the pusher member 130 may terminate in a substantially blunt distal tip 135, e.g., to facilitate contacting, pushing, and/or "cinching" the plug 2 within the puncture, as described further below.

The pusher member 130 may be substantially rigid, semi-rigid, and/or substantially flexible, having sufficient column strength to allow proximal movement of the cartridge 120 relative to the plug 2 without buckling the pusher member 130. The pusher member 130 may also include a lumen 136 extending between the proximal end 132 and the distal end 134, e.g., to accommodate the positioning member 140, a guidewire (not shown), a flowable sealing compound, and/or other fluid.

The plug 2 may be disposed within the lumen 126 of the cartridge 120 proximate to the distal end 124, e.g., immediately adjacent the distal tip 125. The lumen 126 may be sized such that the plug 2 is slidable therein, e.g., able to traverse distally from the cartridge 120 during delivery, as described further below. The anchoring element 102 may also be disposed within the lumen 126 of the cartridge 120 proximal to the plug 2, e.g., immediately adjacent the plug 2.

In the embodiment shown in FIG. 1, the positioning member 140 may be a guidewire and/or other solid or hollow elongate body, including a proximal end 142, a distal end 144, and a positioning element 146 on the distal end 144. The positioning element 146 may be an expandable element, such as a wire mesh structure, an expandable frame, and/or a balloon member (not shown). Optionally, the positioning element 146 may include a skin or other covering (not shown) on at least a proximal portion thereof, thereby making the positioning element 146 substantially nonporous.

The positioning element 146 may be selectively expandable, e.g., using a pull wire, a source of inflation media (e.g., coupled to a lumen, not shown, extending through the positioning member 140 to a balloon or other inflatable positioning element, also not shown), or other actuator (also not shown) operable from the proximal end 142 of the positioning member 140. Alternatively, the positioning element 146 may be biased to an enlarged condition, but may be compressed to a contracted condition, e.g., by an overlying sleeve or other constraint (not shown). The constraint may be removed to expose the expandable element, allowing the expandable element to automatically expand to the enlarged condition. Additional information on expandable structures that may be incorporated into positioning member 140 may be found in U.S. Pat. Nos. 6,238,412 and 6,635,068, in co-pending applications Ser. No. 10/143,514, published as Publication No. US 2003/0078616 A1, and Ser. No. 10/975,205, filed Oct. 27, 2004 and entitled "Apparatus and Methods for Delivering Sealing Materials During a Percutaneous Procedure to Facilitate Hemostasis" . The entire disclosures of these references are expressly incorporated herein by reference.

Turning to FIGS. 2A and 2B, the delivery apparatus 101 may be used to position and deliver the plug 2 within a puncture, e.g., extra-vascularly just above or otherwise adjacent to an arteriotomy in a blood vessel or other body lumen communicating with the puncture, as explained further below. In one embodiment, as shown in FIG. 2A, the cartridge 120 (along with the pusher member 130, plug 2, and anchoring element 102) may be initially provided on a proximal end 142 of the positioning member 140. The cartridge 120 may be slidable distally along the positioning member 140, e.g., until the distal end 124 of the cartridge 120 is disposed adjacent the positioning element 146, as shown in FIG. 2B.

Optionally, the positioning member 140 and/or pusher member 130 may include one or more detents that engage when the cartridge 120 reaches a predetermined location along the positioning member 140, e.g., to limit subsequent movement of the pusher member 130 relative to the positioning member 140. For example, as shown in FIGS. 2A and 2B, the positioning member 140 may include a ring, tab, or other raised element 145, and the pusher member 130 may include a living hinge, tab, or other latch element 137, e.g., on proximal end 132.

For example, the latch element 137 may simply be an annular notch in the proximal end 132 of the pusher member 130 to bias the proximal end 132 inwardly. The ring 145 may be provided at a predetermined location on the positioning member 140, e.g., a predetermined distance from the positioning element 146 that corresponds to a length of the pusher member 130. As the cartridge 120 (and consequently the pusher member 130) is advanced, e.g., until the plug 2 is disposed adjacent the positioning element 146, the latch element 137 may pass freely over the raised element 145. Thereafter, the latch element 137 may prevent the pusher member 130 from being retracted again past the ring 145, due to the blunt edge of the latch element 137 abutting the ring 145 on the positioning member 140.

Alternatively, the cartridge member 120 and pusher member 130 may be provided initially adjacent the distal end 144 of the positioning member 140, as shown in FIG. 2B. In this alternative, the pusher member 130 and positioning member 140 may include the cooperating detents 133, 145 to prevent proximal movement of the pusher member 130 relative to the positioning member 140. Alternatively, the pusher member 130 may be otherwise fixed relative to the positioning member 140, for example, mechanically bonded, chemically bonded, and the like. Thus, the distal end 134 of the pusher member 130 may be fixed a predetermined distance proximal to the positioning element 146, e.g., to provide the plug 2 immediately adjacent the positioning element 146, as shown in FIG. 2B.

Figures 3A, 3B:
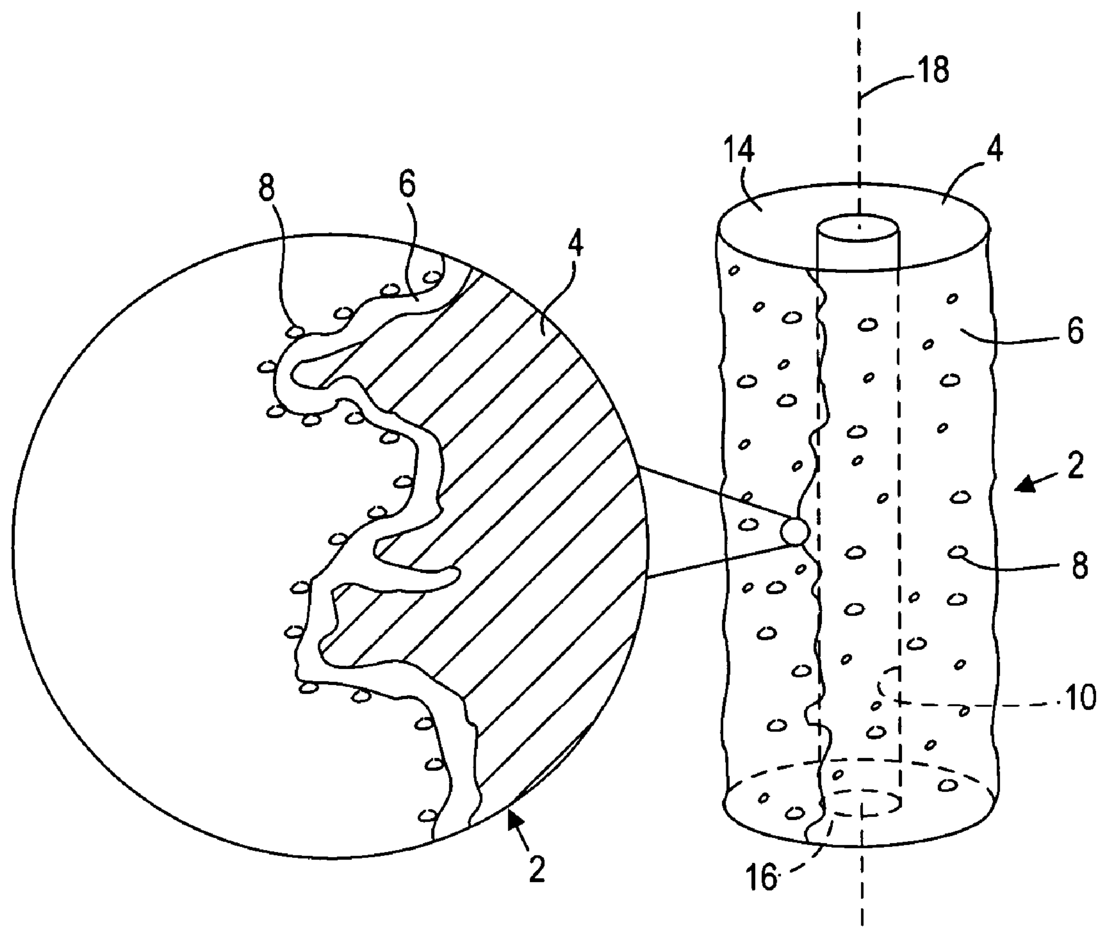
FIG. 3A is a perspective view of an exemplary embodiment of a plug that may be delivered using the apparatus of FIG. 1.
FIG. 3B is a cross-sectional detail of the plug of FIG. 3A.

Turning to FIGS. 3A and 3B, in one embodiment, the plug 2 may include a carrier or core 4, having first and second hydrogel precursors disposed thereon in an unreactive state, thereby providing an adherent coating 6. The plug 2 may have a solid or hollow cylindrical shape, a disk shape, or other shapes or cross-sections, such as elliptical, triangular, square, conical, disk, polygonic shapes, and the like.

As best seen in FIG. 3A, the plug 2 may include a lumen 10 extending between proximal and distal ends 14, 16 thereof, thereby defining a longitudinal axis 18. The lumen 10 may be created when the core 4 is formed, e.g., if the core 4 is rolled from one or more sheets or layers of material or formed by molding. Alternatively, the lumen 10 may formed by boring into or otherwise removing material from an already formed solid core 4. The lumen 10 may be dimensioned such that the positioning member 140, a guidewire or other instrument (not shown) may slide or otherwise pass through the plug 2.

The core 4 may be formed from a biocompatible and/or bioabsorbable material, for example, a porous, bioabsorbable foam or other solid material. In one embodiment, the core 4 may be formed from a biocompatible and/or bioabsorbable hydrogel, e.g., polyethylene glycol ("PEG"), or other synthetic material. In another embodiment, the core 4 may be formed from a lyophilized (i.e., freeze-dried) PEG polymer that contains hydrolytically degradable chemical groups. The lyophilized PEG polymer, e.g., including a macroporous polymer network, may uptake fluid and expand when exposed to an aqueous environment. The magnitude of expansion or swelling (pre to post hydration) may be significant, e.g., between about two and ten times (2×-10×) its lyophilized size based on volume.

In addition or alternatively, the core 4 may include pro-thrombotic material, e.g., including one or more biological pro-thrombotics, such as collagen, fibrin, carboxymethylcellulose, oxidized cellulose, alginates, gelatin, or other protein-based material, and/or synthetic materials, such as polyglycolic acids (PGA's), polyactides (PLA's), polyvinyl alcohol, and the like. The material of the core 4 may be at least partially absorbed by the body over time, e.g., over a period of days, weeks, or months.

Optionally, the core 4 may include therapeutic and/or pharmaceutical agents, e.g., to promote healing, prevent infection and/or other adverse medical events, and the like. Such agents may be embedded in the core material and/or applied as one or more coatings or layers. In addition, the material of the core 4 may have a substantially uniform composition or the composition may be varied, e.g., along its length and/or within underlying layers within the core 4.

The first and second hydrogel precursors 6 may remain in the unreactive state, e.g., before or until exposure to an aqueous physiological environment. An aqueous physiological environment may exist, for example, inside a puncture track extending through tissue. Blood or other bodily fluids that contact the precursor-laden carrier may initiate a hydrogel forming reaction between the two precursors. The reaction of the hydrogel precursors may form a cross-linked adhesive or tacky coating that may aid in retaining the plug 2 within a puncture after deployment and/or in facilitating hemostasis within the puncture.

The first and second hydrogel precursors 6 may be loaded onto the core 4, e.g., by wicking a mixture of the liquid hydrogel precursors onto the core 4. Depending on the material used, the hydrogel precursors may initially be a solid dehydrated material, e.g., a powder, that may be heated above its melting point to form a liquid suitable for wicking. For example, the first and second hydrogel precursors may be sufficiently mixed before being loaded onto the core 4.

Alternatively, the first and second precursors may be provided in a liquid form into which the core 4 may be dipped, that may be poured onto the core 4, and/or otherwise applied to the core 4 together or successively. For example, the first and second precursors may be dissolved in a solvent that may then be applied to the core 4. In either case, once the first and second hydrogel precursors are loaded onto the core 4, the first and second hydrogel precursors may be in a solid or semi-solid state.

The first hydrogel precursor may include any number of hydrogel precursor materials, such as those disclosed in U.S. Pat. Nos. 6,152,943, 6,165,201, 6,179,862, 6,514,534, 6,379,373, 6,703,047, and in co-pending applications Ser. No. 10/010,715 filed Nov. 9, 2001, Ser. No. 10/068,807 filed Feb. 5, 2002, and Ser. No. 10/454,362, filed Jun. 4, 2003. The disclosures of these references and any others cited therein are expressly incorporated by reference herein. For example, in one embodiment, the first hydrogel precursor may include a four arm, 10 kdalton PEG with reactive ester end groups or an eight arm, 20 kDalton PEG amine. Alternatively, the first hydrogel precursor may include a bioabsorbable star polymer having a complementary cross-linking species such as, for example, an amino acid with reactive end groups, e.g., lysine, dilysine, trilysine, etc.

The second hydrogel precursor may include any number of hydrogel precursor materials, e.g., a material reactive with the first precursor material once exposed within a hydrous or aqueous environment, such as those materials disclosed above and in the references incorporated by reference above. For example, the second precursor may be the other of an eight arm, 20 kDalton PEG amine or a four arm, 10 kDalton PEG ester. Alternatively, the second precursor may be the complementary cross-linking species of a bioabsorbable star polymer, such as an amino acid with reactive end groups, e.g., lysine, dilysine, trilysine, etc.

Optionally, an activating agent 8, e.g., a pH adjusting or activating agent, may also be disposed on the core 4, e.g., to initiate, accelerate, or otherwise enhance the reaction of the precursors 6. For example, the pH activating agent 8 may create a localized change in pH after exposure to a hydrous or aqueous environment. In an exemplary embodiment, the pH activating agent 8 may include solid borate crystals, such as $Na_2B_4O_7.10H_2O$, although different salt-based or other materials that alter the localized pH value may be employed. Alternatively, other pH adjusting agents 8 may be used, such as sodium bicarbonate, and the like.

In one embodiment, the pH activating agent 8 may be loaded onto the core 4 by physically contacting solid borate crystals, powder, or other particles onto the precursor-laden (first and second hydrogel precursors) core. For example, the core 4 may simply be rolled over a pH activating agent 8 with sufficient force to embed the pH activating agent 8 into the exterior surface of the core 4. Alternatively, the pH activating agent 8 may be adhered to the exterior surface of the core 4, e.g., by pressing particles of the pH activating agent 8 into the exterior surface, by using an adhesive (e.g., that is substantially inert or unreactive with the first or second precursors), and the like. Additional information on plugs that may be provided are disclosed in co-pending application Ser. No. 10/982,387, filed Nov. 5, 2004, entitled "Apparatus and Methods for Sealing a Vascular Puncture", the entire disclosure of which is expressly incorporated herein by reference.

In other embodiments, laminate structures may be used for the plug 2, e.g., a sheet including multiple layers of different components, such as one or more of the components described above, may be formed, and the sheet may be rolled into a tubular or solid cylindrical structure. An exemplary embodiment of such a sheet may include three layers, e.g., a first layer of lyophilized hydrogel, a second layer of two-part hydrogel adherent material, and a third layer of lyophilized hydrogel. The layers may be substantially uniform, or one or more of the layers may vary in thickness, e.g., along their lengths. For example, in one embodiment, the layer(s) may become progressively thicker from one edge corresponding to the proximal end 14 of the plug 2 to the opposite edge corresponding to the distal end 16 of the plug 2. Thus, the plug 2 may have a frustoconical shape (not shown), rather than a substantially uniform cylindrical shape.

In another embodiment, a layer of lyophilized hydrogel may be provided, and an adherent layer, e.g., including two hydrogel precursors in an initially unreactive state, may be applied to one surface of the layer of lyophilized hydrogel. A pH adjusting agent, e.g., borate crystals, may be embedded or otherwise applied to the opposite surface of the layer of lyophilized hydrogel. Thus, in this embodiment, the pH adjusting agent may be substantially segregated from the adherent layer. This may be desirable if to prevent the pH adjusting agent from initiating reaction of the materials of the adherent layer prematurely, which may otherwise occur to some degree, even absent an aqueous environment.

In addition or alternatively, the composition of the plug 2 may be varied along its length. For example, material on or adjacent the distal end 16 of the plug 2 may more rapidly rehydrate and/or otherwise expand than material on or adjacent the proximal end 14 of the plug 2. In an exemplary embodiment, a composition of hydrogel may be provided adjacent the distal end 16 that is more porous than the hydrogel provided adjacent the proximal end 14, which may accelerate expansion of the distal end 16 compared to the proximal end 14.

In addition or alternatively, different hydrogel compositions may be used such that the distal end 16 is capable of absorbing more liquid than the proximal end 14, such that the distal end 16 swells to a greater size the proximal end 14. Thus, in its hydrated, final state, the plug 2 may have a frustoconical shape (not shown), or other shape in which the distal end 16 is substantially larger than the proximal end 14. This configuration may facilitate and/or enhance compaction against an arteriotomy or otherwise enhance sealing. In addition or alternatively, the material of the plug 2 may be compacted before or after being formed into the plug shape, e.g., to change its shape from a substantially uniform cylindrical shape and/or to change the density of the plug 2 along its length.

Figure 4:
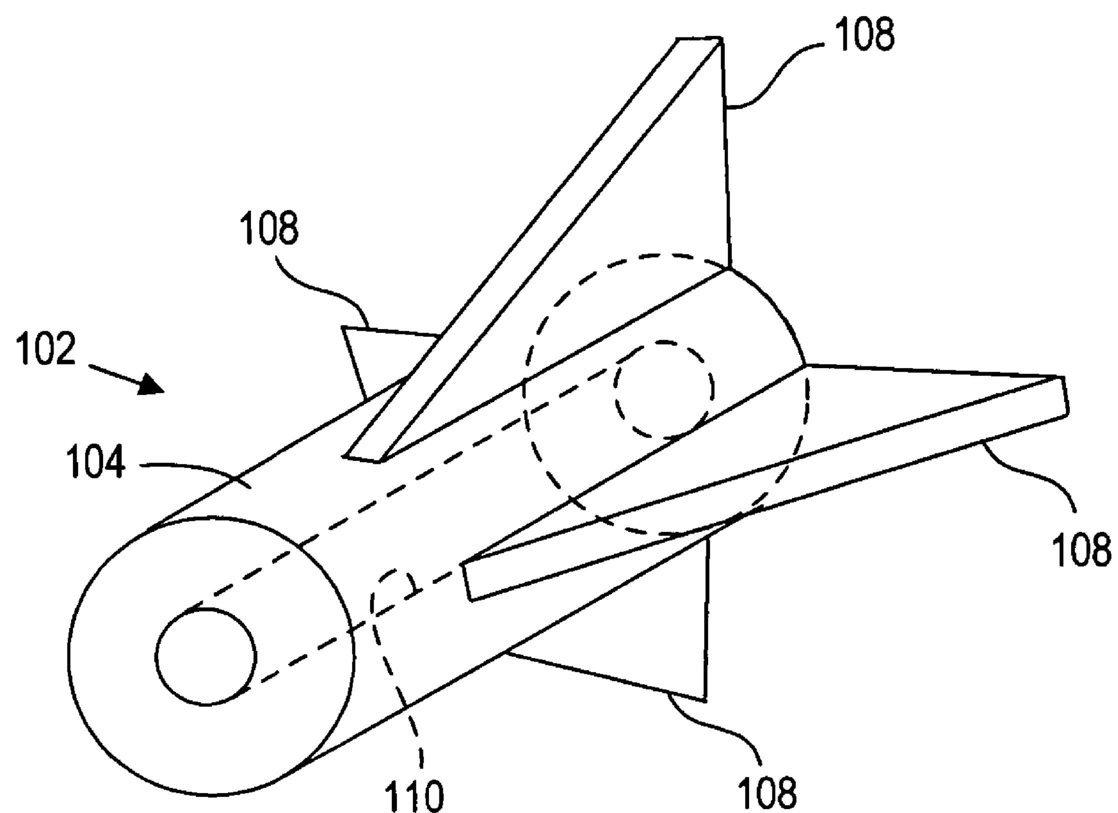
FIG. 4 is a perspective view of an exemplary embodiment of an anchoring element that may be delivered using the apparatus of FIG. 1.

Turning to FIG. 4, an exemplary embodiment of an anchoring element 102 is shown. Generally, the anchoring element 102 includes a body 104 including a lumen 110 and one or more protrusions 108. For example, as shown in FIG. 4, the protrusions 108 include a plurality of barbs extending radially outwardly from the body 104. As shown, the protrusions 108 may extend transversely from the body 104, e.g., laterally and proximally. Thus, when the protrusions 108 are embedded in or otherwise contact surrounding tissue, the protrusions 108 may limit proximal movement of the anchoring element 102.

The anchoring element 102 may be formed from a substantially rigid bioabsorbable material. For example, in one embodiment, the anchoring element 102 may be formed from dehydrated hydrogel material, e.g., air-dried hydrogel. When a hydrogel material is air-dried (as opposed to freeze-dried), the material may collapse in upon itself, e.g., resulting in a substantially nonporous structure that is substantially rigid. The resulting structure may be relatively nonporous, e.g., compared to lyophilized hydrogel, such as those described above for the plug 2. Thus, although capable of rehydrating when exposed to an aqueous environment, the anchoring element 102 may hydrate at a slower rate than the plug 2, e.g., on the order of several minutes.

Because of its rigidity, the material may then be formed into a desired shape, e.g., by laser cutting, sawing, machining, grinding, and the like. Thus, a desired volume of hydrogel may be air-dried, and then the resulting piece of hydrogel may be formed, e.g., to create the body 104, lumen 110, and protrusions 108.

Alternatively, the anchoring element 102 may be formed from other bioabsorbable materials that are sufficiently rigid to engage tissue surrounding a puncture and anchor the anchoring element 102 and plug 2 within the puncture. For example, synthetic materials may be used, such as polyglycolic acids (PGA's), polyactides (PLA's), and polyvinyl alcohol. In further alternatives, the anchoring element 102 may include pro-thrombotic material, e.g., including one or more biological pro-thrombotics, such as collagen, fibrin, carboxymethylcellulose, oxidized cellulose, alginates, gelatin, or other protein-based material.

In a further alternative, the anchoring element 102 may be formed from biocompatible, but not bioabsorbable material. For example, the anchoring element 102 may be formed from metal, such as stainless steel, or plastics, that may remain within a patient's body indefinitely. The anchoring element 102 may be of sufficient size to engage tissue surrounding a puncture, yet be small enough to remain unobtrusively within the patient's body after the procedure, i.e., after the plug 2 has been absorbed and/or the puncture has healed.

Turning to FIGS. 5A-5F, an exemplary method is shown for sealing a puncture 90, e.g., using the apparatus 101 described above to deliver a plug 2 and extra-vascular anchoring element 102, such as any of the embodiments described above. Generally, the puncture 90 extends from a patient's skin 92 through intervening tissue 96, e.g., to a body lumen 94. In an exemplary embodiment, the puncture 90 may be a percutaneous puncture communicating with a blood vessel 94, such as a femoral artery, carotid artery, and the like.

In an exemplary method, the puncture 90 may be created using known procedures, e.g., using a needle, guidewire, one or more dilators, and the like (not shown). An introducer sheath 20 may be advanced through the puncture 90 into the vessel 94, e.g., to provide access into the vessel 90 for one or more instruments, and/or allow one or more diagnostic and/or interventional procedures to be performed via the vessel 90, as is known in the art. Upon completing the procedure(s) via the vessel 94, any instruments and/or the introducer sheath (not shown) may be removed from the puncture 90.

Figure 5A:
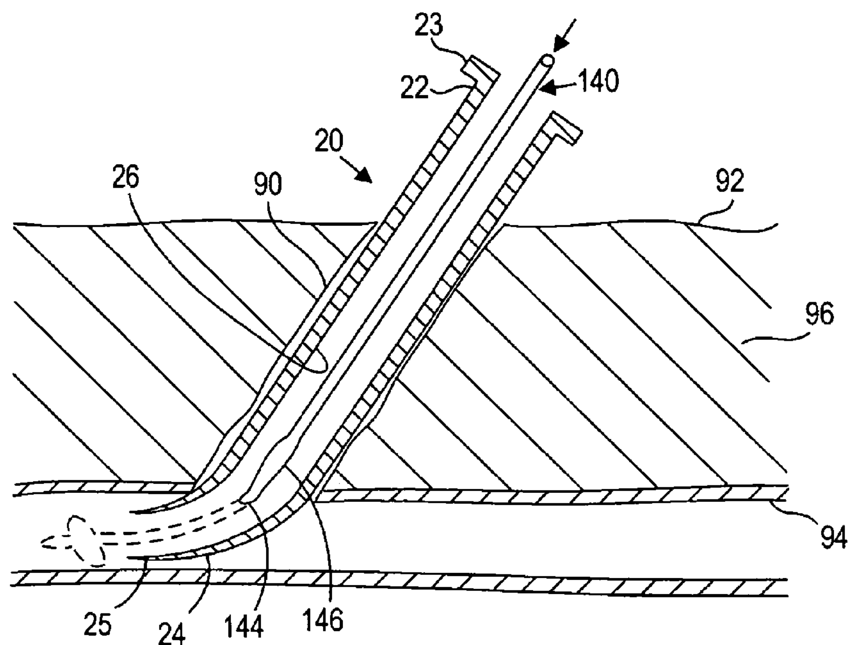
FIGS. 5A-5F are cross-sectional views of a patient's body, showing a method for sealing a puncture extending from the patient's skin to a blood vessel using the apparatus of FIG. 1.

With reference to FIG. 5A, a positioning member 140 may be introduced into and/or through the lumen 26 of the introducer sheath 20, e.g., with the expandable frame or other positioning element 146 thereon in a collapsed condition. The cartridge 120 (along with the plug device 102 and pusher member 130) may be provided initially on the proximal end 142 of the positioning member 140 (not shown in FIG. 5A for clarity, see FIG. 2A). Thus, the cartridge 120 may initially be located outside the puncture 90 as the positioning member 130 is advanced into the puncture 90.

Alternatively, the cartridge 120 may be carried on the distal end 144 of the positioning member 140 (as shown in FIG. 2B), e.g., such that the cartridge 120 (along with the plug device 102 and pusher member 130) are introduced simultaneously with the positioning member 140 (not shown in FIG. 5A). In a further alternative, the cartridge 120 may be provided separate from the positioning member 140 (not shown). After the positioning member 140 is advanced into the puncture 90, the shaft of the positioning member 140 may extend proximally from the proximal end 22 of the introducer sheath 20 out of the puncture 90. The proximal end 142 of the positioning member 140 may be back-loaded into the cartridge 120, e.g., through the lumens 10, 110, 136 of the plug 2, anchoring element 102, and pusher member 130.

Figure 5B:
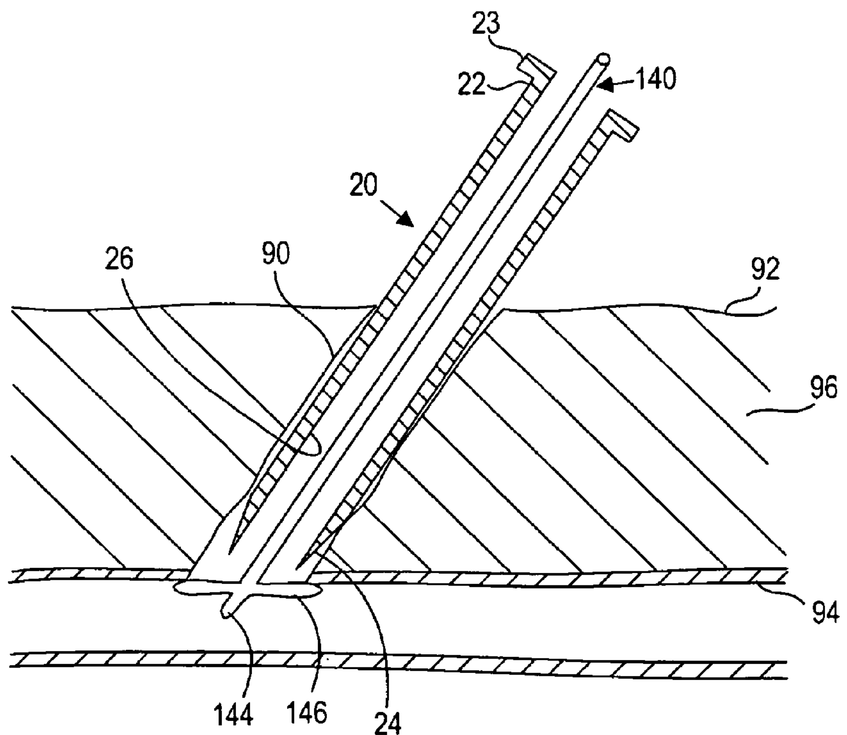

Still referring to FIG. 5A, the distal end 144 of the positioning member 140 may be inserted through the puncture 90 (via the introducer sheath 20) and into the vessel 94 (shown in phantom). Turning to FIG. 5B, once the positioning element 146 is disposed within the vessel 94, i.e., beyond the distal end 24 of the introducer sheath 20, the positioning element 146 on the distal end 144 of the positioning member 140 may be expanded or otherwise deployed to an enlarged condition. After expanding the positioning element 146, the positioning member 140 may be at least partially withdrawn until the positioning element 146 contacts the wall of the vessel 94, e.g., to substantially seal the vessel 94 from the puncture 90.

In an exemplary method, this may involve a two-step process (although it may be completed in a single continuous action). First, with expanded positioning element 146, the positioning member 140 is withdrawn until it contacts the distal end 24 of the introducer sheath 20, which may provide a first tactile feedback to the user (that the positioning element 146 has contacted the introducer sheath 20 based upon the increased weight and/or resistance to proximal movement). The positioning member 140 may be withdrawn further until the positioning element 146 contacts the wall of the vessel 94, thereby providing a second tactile feedback. The introducer sheath 20 may be pulled proximally by the positioning element 146 as the positioning member 120 is withdrawn, e.g., until the distal end 24 of the introducer sheath 20 is withdrawn from the vessel 94 into the puncture 90, as shown in FIG. 5B.

Proximal tension may be applied and/or maintained on the positioning member 140 to hold the positioning element 146 against the wall of the vessel 94, e.g., to seal the puncture 90 from the vessel 94. The proximal tension may be maintained manually or using a tensioner device (not shown) to provide temporary hemostasis, e.g., during the subsequent steps. Exemplary tension devices are disclosed in co-pending application Ser. No. 10/806,952, filed Mar. 22, 2004, the entire disclosure of which is expressly incorporated herein by reference.

Figure 5C:
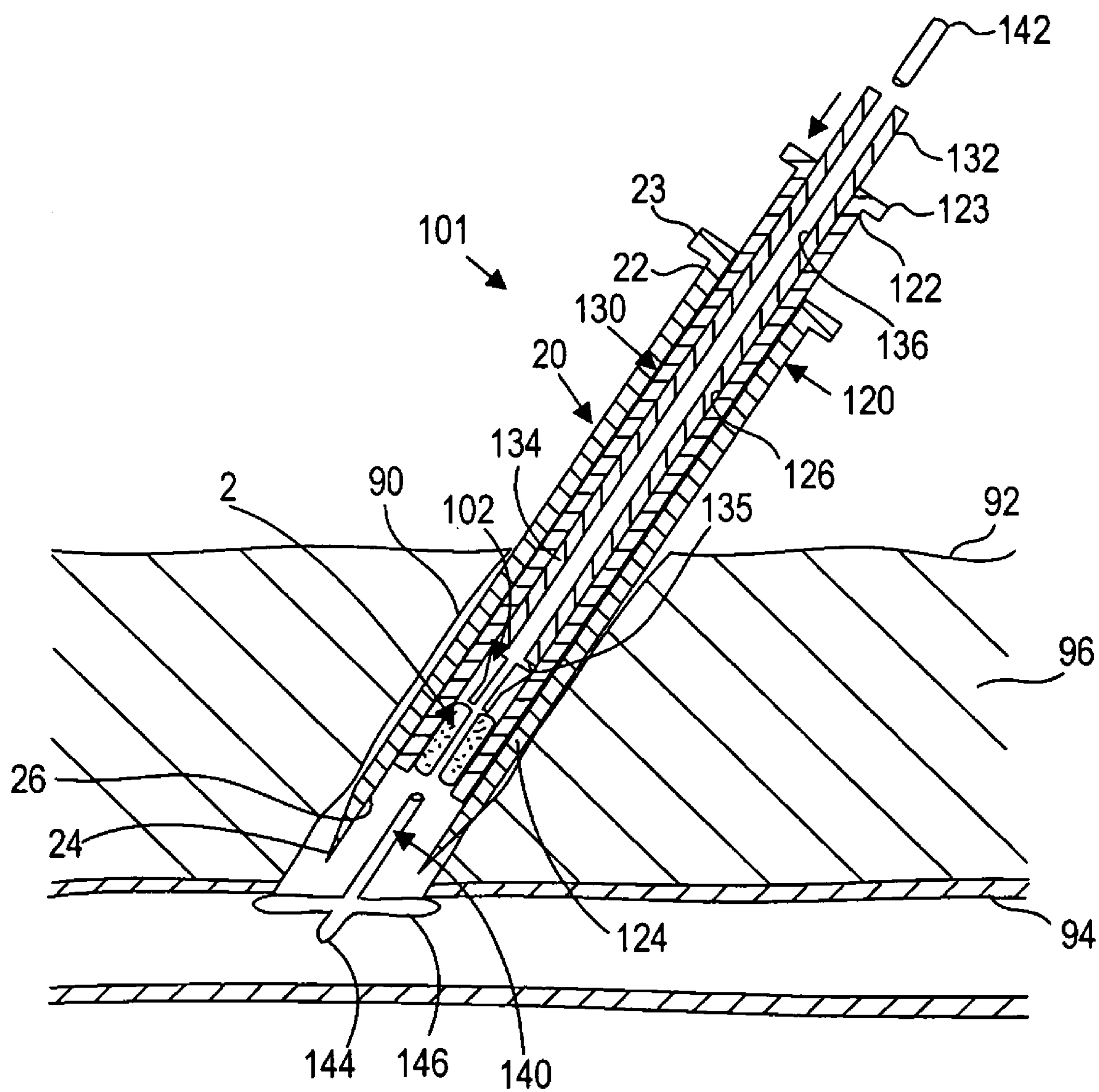

Turning to FIG. 5C, the cartridge 120 (carrying the plug 2 and anchoring element 102) may be advanced distally over the positioning member 140 into the puncture 90. For example, the cartridge 120 may be advanced through the introducer sheath 20 until a hub 123 of the cartridge 120 abuts a hub 23 on the introducer sheath 20, as shown in FIG. 5C. As explained above with reference to FIGS. 2A and 2B, as the cartridge 120 is advanced, the pusher member 130 may slide over the positioning member 140 until the latch element 137 on the pusher member 130 passes over the ring 145 on the positioning member 140. This may prevent subsequent proximal movement of the pusher member 130 relative to the positioning member 140.

Figure 5D:
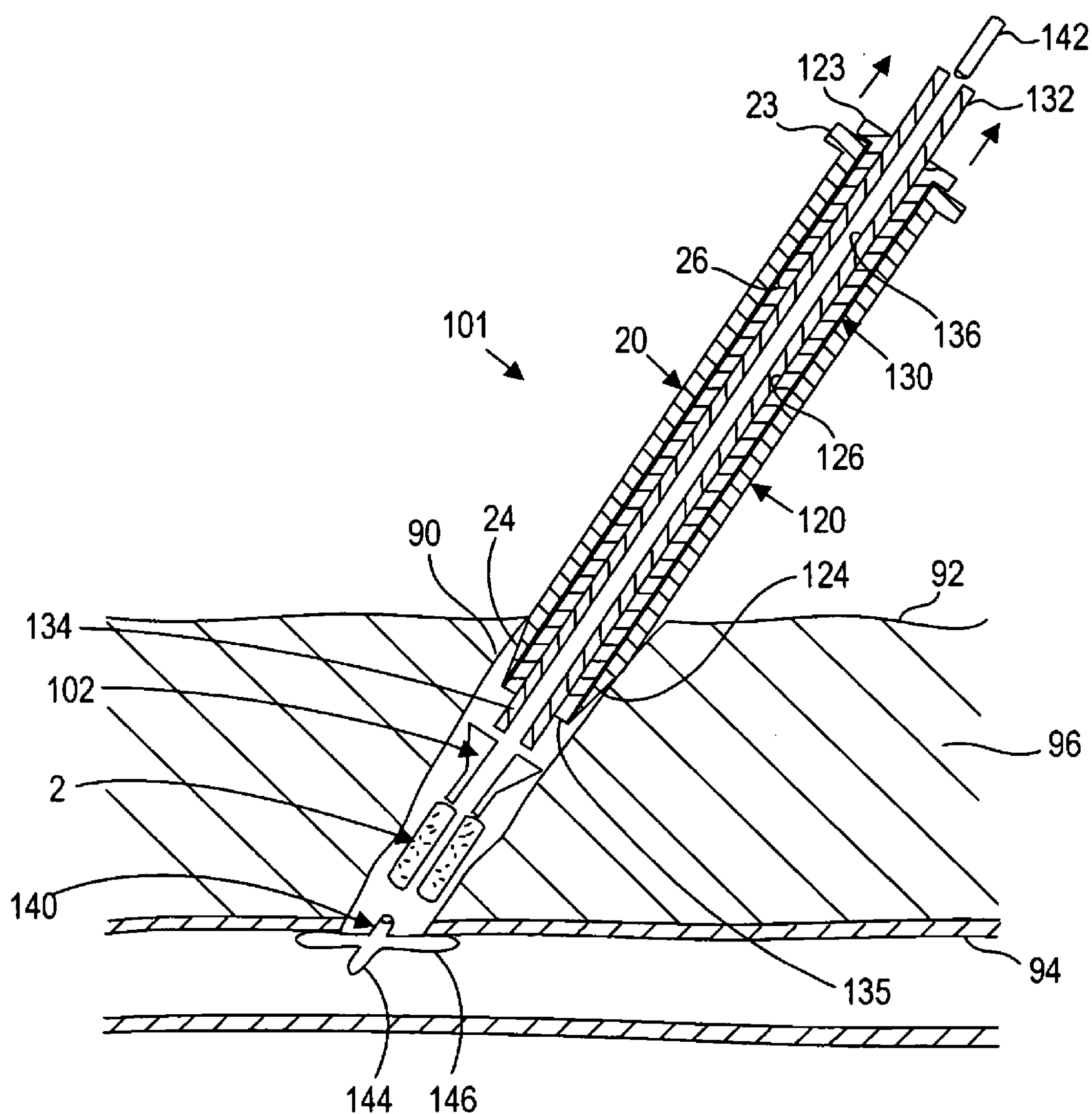

Now referring to FIG. 5D, while proximal tension is maintained on the positioning member 140, the pusher member 130 is maintained with the distal end 134 immediately adjacent the anchoring element 102, and the introducer sheath 20 and cartridge 120 are retracted proximally to expose or otherwise deploy the plug 2 and anchoring element 102 within the puncture 90. The pusher member 130 may serve as a stop that prevents the plug 2 and anchoring element 102 from moving proximally while the introducer sheath 20 and cartridge 120 are withdrawn.

Alternatively, if the pusher member 130 is not provided initially within the cartridge 120, the pusher member 130 may be advanced distally into the lumen 126 of the cartridge 120, e.g., until the distal end 134 of the pusher member 130 is proximally adjacent the anchoring element 102. The cartridge 120 (and introducer sheath 20) may then be withdrawn, while maintaining the pusher member 130 in position to deploy the plug 2 and anchoring element 102 successively within the puncture 90.

In one embodiment, the user of the delivery apparatus 101 may position his or her thumb on hub 133 of the pusher member 130 to maintain its position while the introducer sheath 20 and cartridge 120 are retracted by pulling on hub 23, e.g., using his or her index and middle fingers. For example, as shown in FIG. 5D, with the hub 123 of the cartridge 120 abutting the hub 23 of the introducer sheath 20, the hub 23 of the introducer sheath 20 may be held and withdrawn, thereby causing the cartridge 120 to be withdrawn simultaneously. Alternatively, the introducer sheath 20 may be removed first, and then the cartridge 120 may be removed. The cartridge 120 and introducer sheath 20 may be removed entirely from the puncture 90 or only sufficiently to expose the plug 2 and anchoring element 102 within the puncture 90.

Figure 5E:
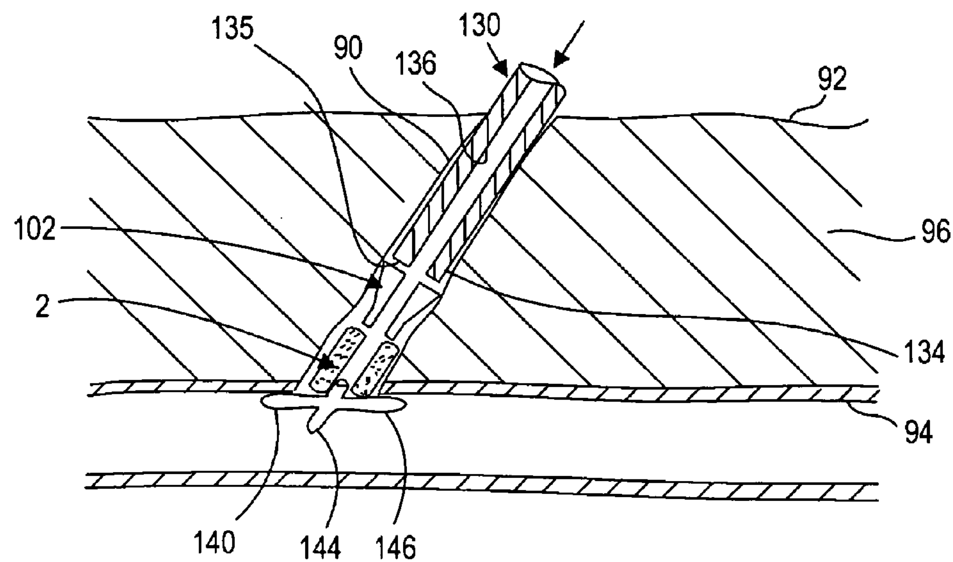

Optionally, as shown in FIG. 5E, the plug 2 may be cinched or otherwise compressed within the puncture 90, e.g., by advancing the pusher member 130 distally to press the anchoring element 102 against the plug 2 and the plug 2 against the wall of the vessel 94 and/or against the positioning element 146. This may cause the plug 2 to expand radially outwardly and/or seal against the arteriotomy, e.g., to enhance sealing the puncture 90 from the vessel 94.

After delivering the plug 2 and anchoring element 102, the proximal tension on the positioning member 140 may be released and/or the positioning element 146 may be collapsed to its collapsed state. For example, the positioning element 146 may be mechanically collapsed or deflated. After the positioning element 146 is collapsed, the positioning member 140 (and consequently the positioning element 146) may be slowly withdrawn through the lumens 10, 110, 136 of the plug 2, the anchoring element 102, and the pusher member 130, respectively.

While the positioning member 140 is withdrawn, the pusher member 130 may be maintained to serve as a stop and prevent proximal migration of the plug 2 and/or anchoring element 102 within the puncture 90. In embodiments where the plug 2 includes an adherent layer (not shown in FIG. 5D), the "sticky" adherent layer may also aid in securing the plug to the tissue surrounding the puncture 90 to prevent migration. In addition or alternatively, the protrusions 108 on the anchoring element 102 may engage the surrounding tissue to prevent migration of the plug 2.

After removing the positioning member 140, the pusher member 130 may be withdrawn, leaving the plug 2 and anchoring element 102 in place. If desired, e.g., if bleeding occurs proximally through the lumen 136 of the pusher member 130, liquid hydrogel or other sealing compound may be delivered into the puncture 90 above and/or around the plug device 102, to assist in achieving permanent hemostasis.

Figure 5F:
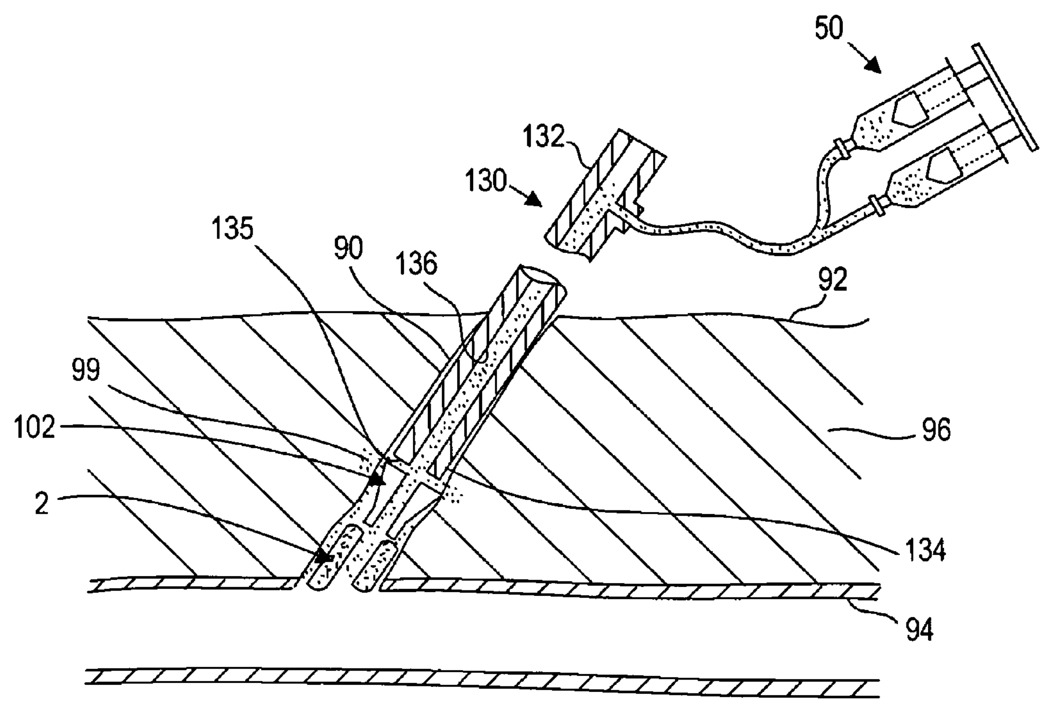

For example, as shown in FIG. 5F, a source of sealing compound, e.g., a syringe assembly 50 carrying liquid sealing compound components, may be coupled to the proximal end 132 of the pusher member 130 and sealing compound 99 may be delivered into the puncture 90 above and/or around the plug 2 and/or anchoring element 102. Optionally, the pusher member 130 may be retracted proximally as the sealing compound 99 is delivered to at least partially fill the puncture 90 with the sealing compound 99.

When the positioning element 146 is collapsed and/or removed, blood and/or other fluid within the vessel 94 may enter the puncture 90, thereby exposing the plug 2 and anchoring element 102 to an aqueous physiological environment. The aqueous physiological environment may wet the plug 2 and anchoring element 102, thereby initiating rehydration of the materials of the plug 2 and/or anchoring element 102 and/or initiating a reaction between the first and second precursors (or other adherent coating) on the plug 2.

For example, with additional reference to FIG. 3, the fluid may dissolve the activating agent 8, changing the pH of the fluid to initiate the first and second hydrogel precursors 6 reacting with one another. The reaction of the first and second hydrogel precursors 6 may form an adhesive or "sticky" hydrogel coating that may bond or otherwise attach to tissue surrounding the puncture 90, which may facilitate retaining the plug 2 in place within the puncture 90. In addition, if the plug 2 includes lyophilized hydrogel, the hydrogel may expand or swell as it hydrates to further aid in retaining the plug 2 within the puncture 90 and/or enhance sealing the puncture 90.

In one embodiment, the plug 2 and anchoring element 102 both include dehydrated hydrogel, the plug 2 including lyophilized hydrogel, and the anchoring element 102 including air-dried hydrogel. In this embodiment, because the anchoring element 102 is less porous, it does not hydrate as rapidly as the plug 2. This may be desirable to ensure that the anchoring element 102 retains its rigidity and shape initially, e.g., for the several minutes or hours it takes for the anchoring element 102 to hydrate. The plug 2 may hydrate and expand more rapidly than the anchoring element 102, e.g., within seconds or minutes to enhance sealing of the puncture 90.

Because the anchoring element 102 may retain its shape and rigidity for several minutes or even hours after being delivered, the protrusions 108 of the anchoring element 102 may engage the surrounding tissue (particularly as the tissue recoils inwardly into the puncture 90), thereby preventing the anchoring element 102 from moving proximally (and optionally distally) within the puncture 90. With the anchoring element 102 secured within the puncture 90, the plug 2 may be unable to move proximally within the puncture 90, but instead may contact the anchoring element 102. Thus, the anchoring element 102 may prevent the plug 2 from moving away from the arteriotomy, e.g., if the patient becomes ambulatory or is otherwise moved in a manner that may otherwise disturb the plug 2.

The material of the plug 2 and anchoring element 102 may be at least partially absorbed by the body over time, e.g., over a period of days, weeks, or months, as is known in the art. Additional methods for delivering the plug 2 and anchoring element 102 are disclosed in co-pending application Ser. No. 10/982,387, incorporated by reference above. Although this application does not disclose an extra-vascular anchoring element, it will be appreciated that similar methods may be used to deliver both the plug 2 and the anchoring element 102 as those used to deliver the plug 2 alone.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for sealing a puncture extending through tissue, comprising:

a tubular member comprising a proximal end, a distal end sized for insertion through the puncture, a lumen extending between the proximal and distal ends, and a distal opening in communication with the lumen;

a bioabsorbable plug disposed within the lumen and comprising a lumen extending between proximal and distal ends thereof, the plug comprising hydrogel;

a bioabsorbable anchor element disposed within the lumen proximal to the plug;

a pusher member slidable within the lumen of the tubular member for deploying the plug and anchor element through the lumen and out the distal opening of the tubular member; and an elongate positioning member, the positioning member having an expandable element on a distal end thereof, the positioning member sized for slidably passing through the lumen of the tubular member and the lumen of the plug.

2. The apparatus of claim 1, the pusher member comprising a lumen for receiving the positioning member therethrough.

3. The apparatus of claim 1, the anchoring element comprising a lumen for receiving the positioning member therethrough.

4. The apparatus of claim 1, the plug comprising lyophilized hydrogel.

5. The apparatus of claim 1, wherein the plug comprises pro-thrombotic material.

6. The apparatus of claim 1, the plug comprising an elongate body having a disk shape, a solid cylindrical shape, or a rolled sheet cylindrical shape.

7. The apparatus of claim 1, wherein the plug comprises a proximal end and a distal end, and a composition of the plug varies between the proximal and distal ends such that the distal end expands more rapidly than the proximal end.

8. The apparatus of claim 1, wherein the plug comprises a proximal end and a distal end, and a composition of the plug varies between the proximal and distal ends such that the distal end expands to a larger size than the proximal end when the plug is exposed to an aqueous physiological environment.

9. The apparatus of claim 8, wherein the plug expands into a substantially frustoconical shape when exposed to an aqueous physiological environment.

10. The apparatus of claim 1, the plug comprising one or more sheets of material folded or rolled into an elongate shape comprising a proximal end and a distal end.

11. The apparatus of claim 10, wherein at least one sheet of the one or more sheets has a thickness that varies between a first edge corresponding to the proximal end and a second edge corresponding to the distal end after the one or more sheets are folded or rolled into the elongate shape.

12. The apparatus of claim 11, wherein the thickness of the at least one sheet is thinner at the first edge than at the second edge.

13. The apparatus of claim 10, wherein the plug has a greater density at the distal end than at the proximal end.

14. The apparatus of claim 13, wherein at least one sheet of the one or more sheets is compacted before being folded or rolled into the elongate shape to provide the greater density at the distal end than at the proximal end.

15. The apparatus of claim 1, the anchoring element comprising one or more protrusions for securing the anchoring element to surrounding tissue within a puncture.

16. The apparatus of claim 15, the one or more protrusions comprising a plurality of barbs.

17. The apparatus of claim 1, the anchoring element comprising a substantially rigid body comprising hydrogel.

18. The apparatus of claim 17, the anchoring element comprising substantially nonporous hydrogel.

19. The apparatus of claim 17, the anchoring element comprising air-dried hydrogel.

20. The apparatus of claim 1, the plug and anchoring element comprising material that hydrates when exposed to an aqueous physiological environment, the plug hydrating at a more rapid rate than the anchoring element.

21. The apparatus of claim 1, the plug and anchoring element comprising hydrogel, the plug being more porous than the anchoring element.

22. An apparatus for sealing a puncture extending through tissue and communicating with a body lumen, comprising:

a tubular member comprising a proximal end, a distal end sized for insertion through the puncture, a lumen extending between the proximal and distal ends, and a distal opening communicating with the tubular member lumen, the tubular member defining a longitudinal axis;

a bioabsorbable plug disposed within the lumen of the tubular member adjacent the distal end, the plug further comprising a lumen extending between proximal and distal ends thereof;

a bioabsorbable anchoring element disposed within the lumen of the tubular member proximal to the plug, the anchoring element comprising a lumen extending therethrough;

a pusher member movable within the tubular member lumen for deploying the plug and anchoring element out of the distal opening, the pusher member comprising a lumen extending between proximal and distal ends of the pusher member; and an elongate positioning member comprising a proximal end slidable through the plug lumen, the anchoring element lumen, and the pusher member lumen, the positioning member comprising a positioning element on a distal end thereof that is expandable for preventing the positioning element from being removed from the body lumen into the puncture after being deployed within the body lumen, the positioning element being collapsible to allow the positioning member to be removed from the body lumen after delivering the plug and anchoring element into the puncture.

23. The apparatus of claim 22, the plug comprising lyophilized hydrogel.

24. The apparatus of claim 22, the plug comprising prothrombotic material.

25. The apparatus of claim 22, wherein the plug comprises an elongate body having a disk shape, a solid cylindrical shape, or a rolled sheet cylindrical shape.

26. The apparatus of claim 22, the anchoring element comprising one or more protrusions for securing the anchoring element to surrounding tissue within a puncture.

27. The apparatus of claim 22, wherein the anchoring element comprising a substantially rigid body comprising substantially nonporous hydrogel.

28. The apparatus of claim 22, the anchoring element comprising air-dried hydrogel.

29. The apparatus of claim 22, the plug and anchoring element comprising material that hydrates when exposed to an aqueous physiological environment, the plug hydrating at a more rapid rate than the anchoring element.

30. The apparatus of claim 22, the plug and anchoring element comprising hydrogel, the plug being more porous than the anchoring element.

31. The apparatus of claim 22, wherein the positioning member and the pusher member comprise cooperating elements that limit relative movement of the pusher member relative to the positioning member.

32. The apparatus of claim 31, wherein the tubular member and pusher member are movable from a proximal end of the positioning member towards the distal end of the positioning member, the cooperating elements engaging when the pusher member reaches a predetermined distal location to prevent further proximal movement of the pusher member beyond the predetermined distal location.

33. An apparatus for sealing a puncture extending through tissue and communicating with a body lumen, comprising:

an elongate positioning member comprising a proximal end, a distal end sized for introduction into a puncture, and a positioning element on the distal end thereof that is movable between a contracted condition allowing introduction through a puncture into a body lumen and an enlarged condition preventing the positioning element from being removed from the body lumen;

a tubular member comprising a proximal end, a distal end sized for insertion through the puncture, and a lumen extending between the proximal and distal ends slidably receiving the positioning member therethrough allowing the tubular member to be advanced over the positioning member;

a bioabsorbable plug disposed within the lumen of the tubular member adjacent the distal end;

a bioabsorbable anchoring element disposed within the lumen of the tubular member proximal to the plug; and a pusher member within the tubular member lumen for deploying the plug and anchoring element out of the tubular member distal end, wherein the pusher member, anchoring element, and plug comprise lumens for slidably receiving the positioning member therethrough such that the pusher member, anchoring element, and plug are advanceable over the positioning member when the tubular member is advanced over the positioning member and for allowing the positioning member to be removed from the puncture with the positioning element in the contracted condition after the plug and anchoring element are delivered into the puncture.

34. The apparatus of claim 33, the plug comprising lyophilized hydrogel.

35. The apparatus of claim 33, the plug comprising prothrombotic material.

36. The apparatus of claim 33, wherein the plug comprises an elongate body having a disk shape, a solid cylindrical shape, or a rolled sheet cylindrical shape.

37. The apparatus of claim 33, the anchoring element comprising one or more protrusions for securing the anchoring element to surrounding tissue within a puncture.

38. The apparatus of claim 33, wherein the anchoring element comprising a substantially rigid body comprising substantially nonporous hydrogel.

39. The apparatus of claim 33, the anchoring element comprising air-dried hydrogel.

40. The apparatus of claim 33, the plug and anchoring element comprising material that hydrates when exposed to an aqueous physiological environment, the plug hydrating at a more rapid rate than the anchoring element.

41. The apparatus of claim 33, the plug and anchoring element comprising hydrogel, the plug being more porous than the anchoring element.

42. The apparatus of claim 33, wherein the positioning member and the pusher member comprise cooperating elements that limit relative movement of the pusher member relative to the positioning member.

43. The apparatus of claim 42, wherein the tubular member and pusher member are movable from a proximal end of the positioning member towards the distal end of the positioning member, the cooperating elements engaging when the pusher member reaches a predetermined distal location to prevent further proximal movement of the pusher member beyond the predetermined distal location.

* * * * *